(12) United States Patent
Brady et al.

(10) Patent No.: US 10,080,575 B2
(45) Date of Patent: Sep. 25, 2018

(54) CLOT REMOVAL DEVICE

(71) Applicant: Neuravi Limited, Galway (IE)

(72) Inventors: Eamon Brady, County Galway (IE);
Brendan Casey, County Galway (IE);
Michael Gilvarry, County Galway
(IE); David Vale, County Galway (IE)

(73) Assignee: Neuravi Limited, Galway (IE)

( * ) Notice: Subject to any disclaimer, the term of this patent is extended or adjusted under 35 U.S.C. 154(b) by 287 days.

(21) Appl. No.: 14/774,078

(22) PCT Filed: Mar. 12, 2014

(86) PCT No.: PCT/EP2014/054826
§ 371 (c)(1),
(2) Date: Sep. 9, 2015

(87) PCT Pub. No.: WO2014/140090
PCT Pub. Date: Sep. 18, 2014

(65) Prior Publication Data
US 2016/0022296 A1 Jan. 28, 2016

Related U.S. Application Data

(60) Provisional application No. 61/780,422, filed on Mar. 13, 2013.

(51) Int. Cl.
*A61B 17/22* (2006.01)
*A61M 29/00* (2006.01)
(Continued)

(52) U.S. Cl.
CPC ...... *A61B 17/22031* (2013.01); *A61B 17/221* (2013.01); *A61B 2017/00309* (2013.01);
(Continued)

(58) Field of Classification Search
CPC .... A61M 29/00; A61F 2/01; A61B 17/22031; A61B 17/221; A61B 17/22; A61B 17/10
See application file for complete search history.

(56) References Cited

U.S. PATENT DOCUMENTS 5,011,488 A 4/1991 Ginsburg
5,092,839 A 3/1992 Kipperman
(Continued)

FOREIGN PATENT DOCUMENTS

DE 10 2010 014778 A1 10/2011
WO WO 94/24926 11/1994
(Continued)

OTHER PUBLICATIONS

US 6,348,062, 02/2002, Hopkins (withdrawn)
(Continued)

*Primary Examiner* — Victor Nguyen
(74) *Attorney, Agent, or Firm* — Troutman Sanders LLP

(57) ABSTRACT

A clot retrieval system comprises a clot retrieval device, a catheter 51, and a tubular shield element 61. The clot retrieval device comprises an elongate member 53 having a proximal end and a distal end, and a clot engaging element 54 at the distal end of the elongate member 53 the clot engaging element 54 having a collapsed delivery configuration and an expanded deployed configuration. The catheter is adapted for placement at a location at which a distal end of the catheter is proximal of the clot engaging element and the tubular shield element 61 extends over the elongate member 53 and is adapted for location between the distal end of the catheter and the proximal end of the clot engaging element 54. The tubular shield element 61 is movable relative to the elongate member 54 when the clot engaging element is in the expanded configuration in that the force that is applied on retraction of the elongate member is spread over the outer surface of the tubular shield element. The
(Continued)

force that would usually be exerted on vessels on retrieval of the clot engaging element is spread by the shield element thus reducing the effects of abrasion.

13 Claims, 9 Drawing Sheets

(51) Int. Cl.
*A61B 17/221* (2006.01)
*A61B 17/00* (2006.01)
*A61B 90/00* (2016.01)

(52) U.S. Cl.
CPC .............. *A61B 2017/00336* (2013.01); *A61B 2017/00853* (2013.01); *A61B 2017/00858* (2013.01); *A61B 2017/22001* (2013.01); *A61B 2017/2215* (2013.01); *A61B 2090/08021* (2016.02)

(56) References Cited

U.S. PATENT DOCUMENTS

| | | |
|---|---|---|
| 5,122,136 A | 6/1992 | Guglielmi et al. |
| 5,171,233 A | 12/1992 | Amplatz |
| 5,234,437 A | 8/1993 | Sepetka |
| 5,387,219 A | 2/1995 | Rappe |
| 5,387,226 A | 2/1995 | Miraki |
| 5,449,372 A | 9/1995 | Schmaltz |
| 5,624,461 A | 4/1997 | Mariant |
| 5,639,277 A | 6/1997 | Mariant |
| 5,645,558 A | 7/1997 | Horton |
| 5,658,296 A | 8/1997 | Bates |
| 5,713,853 A | 2/1998 | Clark |
| 5,769,871 A | 6/1998 | Mers Kelly |
| 5,779,716 A | 7/1998 | Cano |
| 5,810,874 A | 9/1998 | Lefebvre |
| 5,895,398 A | 4/1999 | Wensel |
| 5,897,567 A | 4/1999 | Ressemann |
| 5,904,698 A | 5/1999 | Thomas et al. |
| 5,911,725 A | 6/1999 | Boury |
| 5,935,139 A | 8/1999 | Bates |
| 5,947,995 A | 9/1999 | Samuels |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,102,932 A | 8/2000 | Kurz |
| 6,129,739 A | 10/2000 | Khosravi |
| 6,146,404 A | 11/2000 | Kim |
| 6,165,194 A | 12/2000 | Denardo |
| 6,165,199 A | 12/2000 | Barbut |
| 6,168,604 B1 | 1/2001 | Cano |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,238,412 B1 | 5/2001 | Dubrul |
| 6,245,087 B1 | 6/2001 | Addis |
| 6,251,122 B1 | 6/2001 | Tsukernik |
| 6,264,663 B1 | 7/2001 | Cano |
| 6,312,444 B1 | 11/2001 | Barbut |
| 6,348,056 B1 | 2/2002 | Bates |
| 6,350,271 B1 | 2/2002 | Kurz et al. |
| 6,383,206 B1 | 5/2002 | Gillick |
| 6,402,771 B1 | 6/2002 | Palmer |
| 6,416,541 B2 | 7/2002 | Denardo |
| 6,436,112 B2 | 8/2002 | Wensel |
| 6,458,139 B1 | 10/2002 | Palmer |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,530,935 B2 | 3/2003 | Wensel |
| 6,530,939 B1 | 3/2003 | Hopkins |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |
| 6,610,077 B1 | 8/2003 | Hancock et al. |
| 6,616,679 B1 | 9/2003 | Khosravi |
| 6,632,241 B1 | 10/2003 | Hancock et al. |
| 6,638,245 B2 | 10/2003 | Miller |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,730,104 B1 | 5/2004 | Sepetka |
| 6,824,545 B2 | 11/2004 | Sepetka |
| 6,855,155 B2 | 2/2005 | Denardo et al. |
| 6,878,163 B2 | 4/2005 | Denardo et al. |
| 6,913,612 B2 | 7/2005 | Palmer |
| 6,913,618 B2 | 7/2005 | Denardo et al. |
| 6,953,472 B2 | 10/2005 | Palmer et al. |
| 6,989,019 B2 | 1/2006 | Mazzocchi |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,175,655 B1 | 2/2007 | Malaei |
| 7,179,273 B1 | 2/2007 | Palmer et al. |
| 7,220,271 B2 | 5/2007 | Clubb |
| 7,288,112 B2 | 10/2007 | Denardo et al. |
| 7,306,618 B2 | 12/2007 | Demond |
| 7,323,001 B2 | 1/2008 | Clubb |
| 7,410,491 B2 | 8/2008 | Hopkins |
| 7,452,496 B2 | 11/2008 | Brady et al. |
| 7,534,252 B2 | 5/2009 | Sepetka |
| 7,556,636 B2 | 7/2009 | Mazzocchi |
| 7,594,926 B2 | 9/2009 | Linder |
| 7,618,434 B2 | 11/2009 | Santra |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,828,815 B2 | 11/2010 | Mazzocchi |
| 7,846,176 B2 | 11/2010 | Mazzocchi |
| 7,850,708 B2 | 12/2010 | Pal |
| 7,922,732 B2 | 4/2011 | Mazzocchi |
| 7,927,784 B2 | 4/2011 | Simpson |
| 7,931,659 B2 | 4/2011 | Bose et al. |
| 8,043,326 B2 | 10/2011 | Hancock et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,137,377 B2 | 3/2012 | Palmer et al. |
| 8,142,422 B2 | 3/2012 | Makower et al. |
| 8,357,178 B2 | 1/2013 | Grandfield et al. |
| 8,366,663 B2 | 2/2013 | Fiorella et al. |

(56) References Cited

U.S. PATENT DOCUMENTS

| | | |
|---|---|---|
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,777,976 B2 * | 7/2014 | Brady .............. A61B 17/22031 606/127 |
| 8,784,441 B2 | 7/2014 | Rosenbluth et al. |
| 2001/0001315 A1 | 5/2001 | Bates |
| 2001/0016755 A1 | 8/2001 | Addis |
| 2001/0051810 A1 | 12/2001 | Dubrul |
| 2002/0016609 A1 | 2/2002 | Wensel |
| 2002/0022859 A1 | 2/2002 | Hogendijk |
| 2002/0026211 A1 | 2/2002 | Khosravi |
| 2002/0052620 A1 | 5/2002 | Barbut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0123765 A1 | 9/2002 | Sepetka |
| 2002/0156455 A1 | 10/2002 | Barbut |
| 2002/0161393 A1 | 10/2002 | Demond |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0050663 A1 | 3/2003 | Khachin |
| 2003/0144687 A1 | 7/2003 | Brady et al. |
| 2003/0153944 A1 | 8/2003 | Phung |
| 2003/0163064 A1 | 8/2003 | Vrba |
| 2003/0171769 A1 | 9/2003 | Barbut |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0236533 A1 | 12/2003 | Wilson |
| 2004/0068288 A1 | 4/2004 | Palmer et al. |
| 2004/0073243 A1 | 4/2004 | Sepetka |
| 2004/0079429 A1 | 4/2004 | Miller |
| 2004/0133231 A1 | 7/2004 | Maitland |
| 2004/0138692 A1 | 7/2004 | Phung |
| 2004/0153118 A1 | 8/2004 | Clubb |
| 2005/0033348 A1 | 2/2005 | Sepetka |
| 2005/0049619 A1 | 3/2005 | Sepetka |
| 2005/0049669 A1 | 3/2005 | Jones |
| 2005/0055033 A1 | 3/2005 | Leslie et al. |
| 2005/0055047 A1 | 3/2005 | Greenhalgh |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0125024 A1 | 6/2005 | Sepetka |
| 2005/0171566 A1 | 8/2005 | Kanamaru |
| 2005/0216030 A1 | 9/2005 | Sepetka |
| 2005/0216050 A1 | 9/2005 | Sepetka |
| 2005/0267491 A1 | 12/2005 | Kellett et al. |
| 2005/0288686 A1 | 12/2005 | Sepetka |
| 2006/0058836 A1 | 3/2006 | Bose |
| 2006/0058837 A1 | 3/2006 | Bose |
| 2006/0058838 A1 | 3/2006 | Bose |
| 2006/0155305 A1 | 7/2006 | Freudenthal |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2007/0156170 A1 | 7/2007 | Hancock |
| 2007/0165170 A1 | 7/2007 | Fukuda |
| 2007/0198028 A1 | 8/2007 | Miloslavski |
| 2007/0198051 A1 | 8/2007 | Clubb et al. |
| 2007/0208367 A1 | 9/2007 | Fiorella |
| 2007/0208371 A1 | 9/2007 | French |
| 2007/0225749 A1 | 9/2007 | Martin |
| 2007/0244505 A1 | 10/2007 | Gilson et al. |
| 2008/0086190 A1 | 4/2008 | Ta |
| 2008/0091223 A1 | 4/2008 | Pokorney |
| 2008/0109031 A1 | 5/2008 | Sepetka |
| 2008/0109032 A1 | 5/2008 | Sepetka |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0200946 A1 | 8/2008 | Braun |
| 2008/0215077 A1 | 9/2008 | Sepetka |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0275493 A1 | 11/2008 | Farmiga |
| 2008/0312681 A1 | 12/2008 | Ansel |
| 2009/0024157 A1 | 1/2009 | Anukhin |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0292297 A1 | 11/2009 | Ferrere |
| 2009/0292307 A1 | 11/2009 | Razack |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnett et al. |
| 2010/0268265 A1 | 10/2010 | Krolik et al. |
| 2010/0318178 A1 | 12/2010 | Rapaport et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0054514 A1 | 3/2011 | Arcand |
| 2011/0054516 A1 | 3/2011 | Keegan |
| 2011/0060359 A1 | 3/2011 | Hannes |
| 2011/0054504 A1 | 5/2011 | Wolf et al. |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0202088 A1 | 8/2011 | Eckhouse et al. |
| 2011/0213403 A1 | 9/2011 | Aboytes |
| 2011/0224707 A1 | 9/2011 | Miloslavski et al. |
| 2011/0276120 A1 | 11/2011 | Gilson et al. |
| 2012/0041449 A1 | 2/2012 | Eckhouse et al. |
| 2012/0041474 A1 | 2/2012 | Eckhouse et al. |
| 2012/0089216 A1 | 4/2012 | Rapaport et al. |
| 2012/0165858 A1 | 6/2012 | Eckhouse et al. |
| 2012/0165859 A1 | 6/2012 | Eckhouse et al. |
| 2013/0144326 A1 | 6/2013 | Brady et al. |
| 2013/0184739 A1 | 7/2013 | Brady et al. |
| 2013/0197567 A1 | 8/2013 | Brady et al. |
| 2013/0345739 A1 | 12/2013 | Brady et al. |
| 2014/0200608 A1 | 7/2014 | Brady et al. |
| 2014/0277079 A1 | 9/2014 | Vale et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0164523 A1 | 6/2015 | Brady et al. |

FOREIGN PATENT DOCUMENTS

| | | |
|---|---|---|
| WO | WO 97/27808 | 8/1997 |
| WO | WO 99/20335 | 4/1999 |
| WO | WO 99/60933 | 12/1999 |
| WO | WO 99/56801 | 4/2000 |
| WO | WO 01/21077 | 3/2001 |
| WO | WO 2004/056275 A1 | 7/2001 |
| WO | WO 02/02162 | 1/2002 |
| WO | WO 02/11627 | 2/2002 |
| WO | WO 02/43616 | 6/2002 |
| WO | WO 02/070061 | 9/2002 |

(56) References Cited

FOREIGN PATENT DOCUMENTS

| WO | WO 02/094111 | 11/2002 |
|---|---|---|
| WO | WO 03/002006 | 1/2003 |
| WO | WO 03/030751 | 4/2003 |
| WO | WO 03/051448 | 6/2003 |
| WO | WO 2004/028571 A2 | 4/2004 |
| WO | WO 2005/027779 A2 | 3/2005 |
| WO | WO 2006/021407 | 3/2006 |
| WO | WO 2006/031410 | 3/2006 |
| WO | WO 2006/107641 | 10/2006 |
| WO | WO 2007/054307 | 5/2007 |
| WO | WO 2007/068424 | 6/2007 |
| WO | WO 2008/034615 | 3/2008 |
| WO | WO 2008/131116 | 10/2008 |
| WO | WO 2009/076482 | 6/2009 |
| WO | WO 2009/086482 | 7/2009 |
| WO | WO 2010/010545 | 1/2010 |
| WO | WO 2010/046897 A1 | 4/2010 |
| WO | WO 2010/146581 A1 | 12/2010 |
| WO | WO 2011/013556 A1 | 2/2011 |
| WO | WO 2011/095352 A1 | 8/2011 |
| WO | WO 2012/052982 A1 | 4/2012 |
| WO | WO 2012/081020 A1 | 6/2012 |
| WO | WO 2012/120490 A2 | 9/2012 |
| WO | WO 2013/109756 A2 | 7/2013 |

OTHER PUBLICATIONS

International Search Report and Written Opinion of International Application No. PCT/EP2014/054826, dated Jun. 5, 2014 (11 pages).

* cited by examiner

CLOT REMOVAL DEVICE

CROSS REFERENCE TO RELATED APPLICATION

This application is a U.S. national phase entry under 35 U.S.C. § 371 of International PCT Application No. PCT/EP2014/054826, filed on Mar. 12, 2014, which claims priority to U.S. Provisional Application No. 61/780,422, filed on Mar. 13, 2013.

FIELD OF THE INVENTION

This invention relates to endovascular medical devices which are retracted through a portion of the vasculature while in contact with the vessel wall as part of their typical method of use. In particular this invention is of benefit to mechanical thrombectomy devices, vena cava filters, embolic filters, stents and similar devices. For example, it is relevant to clot retrieval devices which are used to retrieve blood clots in the case of ischemic stroke, or in another example, stents which are used to relieve stenosis.

BACKGROUND

Mechanical thrombectomy devices such as clot retrieval devices or stentrievers are frequently used to recanalize blocked cerebral arteries in patients suffering from acute ischemic stroke. The method of use of such a device typically involves positioning a large diameter catheter in a location proximal of the obstructive clot, and then advancing a microcatheter and guidewire together to a location distal of the clot. The guidewire is then withdrawn proximally to allow for the introduction of the clot retrieval device in the collapsed configuration through the microcatheter. A generic clot retrieval device is comprised of an elongate member and a clot engaging body connected to the distal end of the elongate member. The clot retrieval device is advanced distally within the microcatheter until is it situated within the clot. At this stage the microcatheter is withdrawn and the device will expand. As the device expands it engages and captures the clot. Once the clot has been captured by the engaging body of the device, aspiration is typically carried out through the large diameter catheter while the device and the clot are withdrawn towards the large diameter catheter (which may be a guide catheter or a sheath or a distal access catheter). The device and the clot are withdrawn into the large diameter catheter and removed from the vasculature.

The force required to retract the device may have undesired consequences. In order to dislodge the clot from the vessel a force must be applied to it through the stentriever device. This force is effectively applied to the vessel in which the clot is lodged and to the distal vascular bed, placing these vessels in tension and placing the vessels proximal of the clot in compression. Once the clot begins to move there is relative movement between the stentriever device and shaft and the vessel wall. This relative movement can cause abrasion and damage to the endothelia and underlying layers of the vessel wall, which may result in a dissection or perforation, or could give rise to the subsequent formation of thrombus which could then be liberated to create an additional stroke.

The force that must be applied to dislodge and retract the clot is dependent not only on how well lodged the clot is in the vessel, but also on the frictional losses that occur where the stentriever device contacts vessel walls or the inner surface of the catheter through which it passes. Thus it would be advantageous to have the use of a device which acts as a shield between the elongate shaft and the vessel wall. In the preferred embodiment the invention would remain in situ in the vessel as the elongate shaft is being retracted and absorb the tension which would normally be exerted on the shaft and the vessels. Preferably the invention would have a low friction inner surface and a higher friction outer surface. This would allow the shaft to move more fluidly within the device while the device remained in the vessel. The present invention includes these features and improves upon the methods of clot retrieval previously discussed.

SUMMARY OF THE INVENTION

According to the invention there is provided a clot retrieval system comprising:—
   a clot retrieval device;
   a catheter; and
   a tubular shield element
   the clot retrieval device comprising an elongate member having a proximal end and a distal end, and a clot engaging element at the distal end of the elongate member the clot engaging element having a collapsed delivery configuration and an expanded deployed configuration,
   the catheter being adapted for placement at a location at which a distal end of the catheter is proximal of the clot engaging element,
   the tubular shield element extending over the elongate member and being adapted for location between the distal end of the catheter and the proximal end of the clot engaging element and being movable relative to the elongate member when the clot engaging element is in the expanded configuration.

The force that would usually be exerted on vessels on retrieval of the clot engaging element is spread by the shield element thus reducing the effects of abrasion.

In use, there is a gap between the distal end of the catheter and the proximal end of the clot engaging element. The tubular shield element may extend partially across this gap or in some cases fully across the gap. In some cases the shield element extends partially into the distal end of the catheter.

In one embodiment the tubular shield element is slidable relative to the elongate member.

In one case the elongate member comprises a distal stop and a proximal stop to limit the sliding movement of the tubular element.

In one embodiment the tubular shield element comprises a distal abutment surface and a proximal abutment surface.

In one case the tubular shield element comprises an inner lumen and an outer surface, the inner lumen being sized to slide freely over at least a distal portion of the elongate member.

In one embodiment the tubular shield element inner lumen comprises a first material and the tubular element outer surface comprises a second material.

In one case the tubular shield element first material comprises a lower coefficient of friction than the tubular element second material.

In one embodiment the system further comprises a microcatheter for delivery of the clot engaging element in the collapsed configuration.

In one case the lumen of the microcatheter is configured to receive the tubular shield element. The outer diameter of the tubular element may be at least as small as the diameter of the clot engagement element in its collapsed configuration.

The disclosed designs overcome the disadvantages of existing mechanical thrombectomy solutions. In one embodiment a tubular member is slidably disposed on the shaft of a thrombectomy device.

The device captures the clot in the engaging body. Once the clot has been captured the device is withdrawn proximally through the vasculature. The withdrawal of the device places pressure on the surrounding vessels and causes abrasion on the inner walls of the vessels. This is the stage at which the highest loads are applied. However the use of a slider tube reduces these forces. As it is slidably disposed on the elongate shaft of the thrombectomy device and the coefficient of friction between the tube and elongate shaft is lower than that between the slider tube and the vessel, the slider tube remains in situ as the shaft is retracted. The force that the elongate shaft would normally exert on the vessels is spread over the outer surface area of the tube. Therefore there is less friction within the vessels and this reduces the effects of abrasion.

The device reduces the friction within the vessel and it also reduces the overall force required to withdraw the elongate shaft. As the level of friction is reduced the forces of compression on the surrounding vasculature are consequently reduced. The slider tube may contain low diameter regions and/or highly flexible regions as described below and these regions increase the flexibility of the tube and thus further reduce the forces on the neighbouring vascular bed. Therefore the overall force required to remove the clot is reduced, which in turn reduces the forces on the vascular bed. Therefore the key benefit of the present invention is a significant reduction in rubbing of the elongate shaft against vessel walls during the initial dislodgement and refraction of the clot.

The slider tube is preferably of an outer diameter that fits within the lumen of a low profile microcatheter, as this enables the safest and easiest crossing of the obstructive clot during initial access. Typical microcatheters used in this kind of procedure range from an inner lumen size of approximately 0.016" to 0.027", and have a distal end outer diameter of between approximately 0.020" to 0.039". Preferred lower profile microcatheters have a lumen of approximately 0.021" or less and have a distal end outer diameter of approximately 0.033" or less. The slider tube outer diameter is preferably the largest diameter than can move freely through the microcatheter lumen, as a larger diameter slider tube will have a lower vessel wall contact pressure for a given force (and hence be less traumatic to the vessel wall) than would a smaller diameter slider tube. Thus the slider tube outer diameter could be in the range of 0.010" to 0.026", but is preferably at least 0.012" and not more than 0.020", and is most preferably in the range of 0.014" to 0.019".

An additional benefit of the present invention is the prevention of accidental retraction of the clot retrieval device into the distal end of the microcatheter and subsequent loss of the clot. This could occur should a physician attempt to use the microcatheter in the manner of a slider tube, namely withdraw the clot retrieval device as far as the microcatheter and withdraw the microcatheter a little further and so forth. This increases the possibility of the device being withdrawn into the microcatheter and resuming its collapsed configuration and therefore losing control of the clot. If a slider tube is used the microcatheter is withdrawn a significant distance and the slider tube will automatically start to advance proximally with the device once the distal end of the slider tube contacts the shaft. The process functions thus as there is less energy expended as the device shaft slides through the slider tube compared to the slider tube moving through the vessel. This effect is influenced by the difference in the coefficient of friction between the slider tube and shaft and between the slider tube and vessel, and also by the relative lateral stiffnesses of shaft and slider tube.

One embodiment of this invention comprises a system for dislodging an occlusive clot from a first blood vessel segment the system comprising: a clot retrieval device and a clot removal catheter, the clot retrieval device comprising a clot engaging element and an elongate member, the clot engagement element having a collapsed delivery configuration and an expanded configuration for engaging with the clot and for dislodging the clot from the first vessel segment, the elongate member configured to apply a pull force to the clot engaging element to dislodge the clot from the first vessel segment, the clot removal catheter comprising a lumen at its distal end sized to receive said clot and configured to maintain a stable position in a second blood vessel segment, said second blood vessel segment being proximal of and larger in diameter than said first blood vessel segment, a third blood vessel segment between said first and second blood vessel segments, the distal end of the elongate member configured to protect the third blood vessel segment from tractive forces transmitted by the elongate member during clot dislodgement from the first vessel segment.

The system may further comprise an elongate structural element and a slider tube, the slider tube configured to slide relative to the elongate structural element.

In one case the elongate member is configured so that the slider tube slides over a distal section of the elongate structural element.

In one embodiment the slider tube comprises a proximal position and a distal position.

In one case the slider tube can slide freely over the surface of the elongate member between a proximal position and a distal position.

In one embodiment the clot retrieval device is delivered to the occlusion site in the first vessel segment through a catheter and the advancement of the clot retrieval device through the lumen of the delivery catheter biases the slider tube in a proximal position.

In one case the slider tube comprises an inner lumen and an outer surface and the inner lumen is sized to slide freely over at least the surface of a distal portion of the elongate structural element.

In one embodiment the slider tube inner lumen comprises a first material and the slider tube outer surface comprises a second material.

In one case the slider tube first material comprises a lower coefficient of friction than the slider tube second material.

In one embodiment the slider tube comprises a distal abutment surface and a proximal abutment surface.

In one case the elongate structural element comprises a distal stop and a proximal stop to limit the sliding movement of the slider tube.

In one embodiment the proximal stop and/or the distal stop of the elongate structural element comprise an abutment surface, a collar, a tube end, a spring end, a tether, a tapered shaft section, a diameter change, or a surface projection.

In one case the elongate member is at least partially a nitinol material or a stainless steel material.

In one embodiment a distal end of the elongate member is connected to the clot engaging element and the proximal end of the elongate member extends exterior of the patient.

In one case the slider tube encircles the elongate structural element over at least a distal portion of its length.

In one embodiment the tractive forces acting on the third blood vessel segment comprise a combination of normal forces acting on the vessel wall and tangential forces acting along the third blood vessel segment wall.

In one case the tractive forces acting on the third blood vessel segment comprise dynamic forces associated with relative movement between the third segment vessel wall and the elongate member.

In one embodiment the elongate member comprises an elongate structural element and a slider tube the slider tube configured to allow relative movement between the elongate structural element and the slider tube during clot dislodgement.

In one case the system comprises a microcatheter for delivering the clot removal device to the occlusive clot in the first vessel segment, the microcatheter comprising a lumen sized to receive the clot engagement element in its collapsed configuration.

In one embodiment retraction of the microcatheter effects deployment of the clot engagement element.

In one case the microcatheter lumen is configured to slidably receive the slider tube.

In one embodiment the slider tube outer diameter is at least as small as the diameter of the clot engagement element in its collapsed configuration.

Another embodiment of this invention comprises a clot removal device for removing an occlusive clot form a distal blood vessel of a patient, the clot removal device comprising a clot engaging element, an elongate member and a tractive tubular member, the clot engagement element having a collapsed delivery configuration and an expanded configuration for engaging with the occlusive clot and for dislodging the occlusive clot from the distal blood vessel, the elongate member comprising a proximal section, an intermediate section and a distal section, a distal end of the distal section of the elongate member connected to the clot engaging element and the proximal end of the elongate member extending exterior of the patient, the elongate member further configured to transmit a pull force applied by the user to the clot engaging element to dislodge the clot from the distal blood vessel, the tractive tubular member configured to encircle the elongate member over at least a portion of the length of the elongate member distal section, the distal section of the elongate member being slidable and rotatable relative to the tractive tubular member, the elongate member distal section and the tractive tubular member configured to protect the proximal blood vessel from tractive forces transmitted by the elongate member during clot dislodgement from the distal vessel segment.

In one embodiment the tractive tubular member is slidable between a proximal position and a distal position along the distal section of the elongate member.

In one case the tractive tubular member comprises an inner lumen and an outer surface and a proximal abutment surface and a distal abutment surface.

In one embodiment the interface between the elongate member distal end and the tractive tubular member comprises the outer surface of the distal section of the elongate member and the inner surface of the lumen of the tractive tubular member.

In one case the interface between the elongate member distal section and the tractive tubular member is configured to facilitate low friction sliding of the tractive tubular member relative to the elongate member.

In one embodiment the coefficient of friction of the inner surface of the tractive tubular member is less than the coefficient of friction of the outer surface of the tractive tubular member.

The distal section of the elongate member may comprise a polished surface or a buffed surface.

In one case the distal section of the elongate member comprises a longitudinally polished surface or a longitudinally buffed surface In one embodiment the clot removal device is delivered to the occlusion site in the distal blood vessel through a catheter and the advancement of the clot removal device through the lumen of the catheter biases the tractive tubular member towards the proximal end of the elongate member distal section.

In one case the tractive tubular member inner surface comprises a first material and the tractive tubular member outer surface comprises a second material.

In one embodiment the tractive tubular member first material comprises a lower coefficient of friction than the tractive tubular member second material.

In one case the elongate member comprises a distal stop and a proximal stop, said distal and proximal stops configured to limit the distance of sliding of the tractive tubular member.

In one embodiment the proximal stop and/or the distal stop of the elongate member comprise an abutment surface, a collar, a tube end, a spring end, a tether, a tapered shaft section, a diameter change, or a surface projection.

In one case the elongate member is at least partially a nitinol material or a stainless steel material.

In one embodiment the slider tube encircles the elongate member distal section over at least a portion of its length.

In one case the clot removal device comprises a sliding distance, said sliding distance comprising the distance along the elongate member that the tractive tubular element can slide without obstruction.

The sliding distance may be at least as long as the length of the occlusive clot, in some cases the sliding distance is at least 10 mm, the sliding distance is at least 20 mm, wherein the sliding distance is at least 30 mm, wherein the sliding distance is at least 40 mm, wherein the sliding distance is at least 50 mm, or the sliding distance is less than 150 mm.

In one embodiment the tractive forces acting on the proximal blood vessel comprise a combination of normal forces acting on the vessel wall and tangential forces acting along the proximal blood vessel wall.

In one case the tractive forces acting on the proximal blood vessel comprise dynamic forces associated with relative movement between the proximal blood vessel wall and the elongate member.

In one embodiment the clot removal device comprises a microcatheter for delivering the clot removal device to the occlusive clot, the microcatheter comprising a lumen sized to receive the clot engagement element in its collapsed configuration.

In one case retraction of the microcatheter effects deployment of the clot engagement element.

In one embodiment the microcatheter lumen is configured to slidably receive the tractive tubular member.

In one case the tractive tubular member outer diameter is at least as small as the diameter of the clot engagement element in its collapsed configuration.

BRIEF DESCRIPTION OF THE DRAWINGS

The invention will be more clearly understood from the following examples.

DETAILED DESCRIPTION

Specific embodiments of the present invention are now described in detail with reference to the figures, wherein identical reference numbers indicate identical or functionality similar elements. The terms "distal" or "proximal" are used in the following description with respect to a position or direction relative to the treating physician. "Distal" or "distally" are a position distant from or in a direction away from the physician. "Proximal" or "proximally" or "proximate" are a position near or in a direction toward the physician. The invention is applicable to any mechanical thrombectomy clot retrieval device, and a generic design of such a clot retrieval device is shown in the illustrations.

Figure 1A:
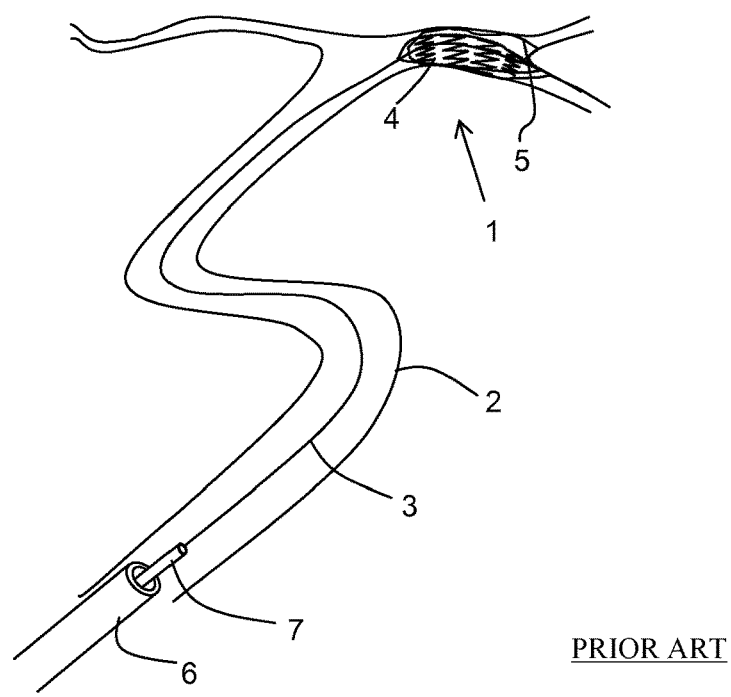
FIG. 1a shows a conventional method for removing a clot.
Figure 1B:
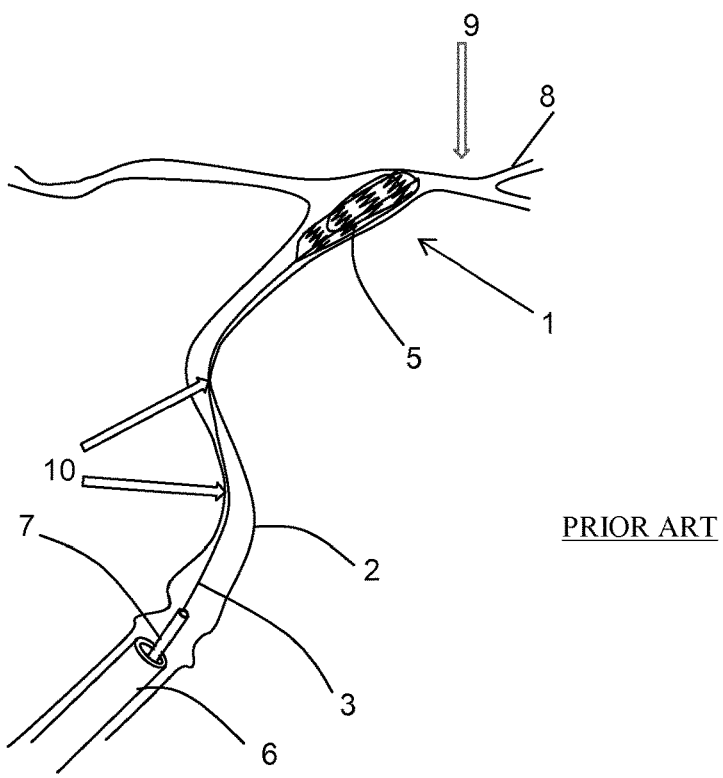
FIG. 1b shows the forces and abrasion on vessels during retraction of clot.

FIG. 1a-b shows the conventional method of retrieving a clot from a tortuous vasculature. A guidewire and microcatheter 7 are inserted into the artery and are advanced across the occlusive clot 5, which is lodged at a bifurcation using any conventionally know techniques.

The guidewire is removed from the microcatheter 7 to allow the clot retrieval device 1 to be advanced in a collapsed configuration until it is located within the clot 5. The device 1 is deployed on retraction of the microcatheter 7. The device comprises an elongate shaft 3, having the distal end that extends interior of the artery and a proximal end that extends exterior of the artery. It has a clot engaging body 4 which is connected to the distal section of the elongate element 3. On expansion, the device exerts a radial force upon the clot and captures the clot against the lumen of the vessel 2.

Once the clot retrieval device has captured the clot, the device is retracted proximally. The force which is pulling the device proximally also exerts a force 9 on the vessels in the immediate vicinity 8 thus pulling these vessels towards the microcatheter 7 and potentially distorting the vasculature in the area as illustrated in FIG. 1b. Furthermore, the proximal force on the device also distorts the vessel 2 in which the elongate member 3 is being retracted. The force compels the vessel 2 to conform to the shape of the elongate member thus forcing it to straighten and lose its original shape. It compresses the vessels in the immediate vicinity of the elongate member 3. In addition, the elongate member 3 may cause abrasion 10 within the lumen of the vessel 2 as it is retracted. As the vessel 2 distorts the elongate member 3 is forced to contact the walls of the vessel which may cause the vessel to lose or damage the endothelia of the vessel at these points.

The vessel distortion and abrasion could be avoided by leaving the microcatheter 7 more distal (and closer to the clot retrieval device) when initially retracting the clot retrieval device, however this could easily result in the user retracting the clot retrieval device, thus collapsing the device within the microcatheter 7 and liberating the clot.

Figure 2:
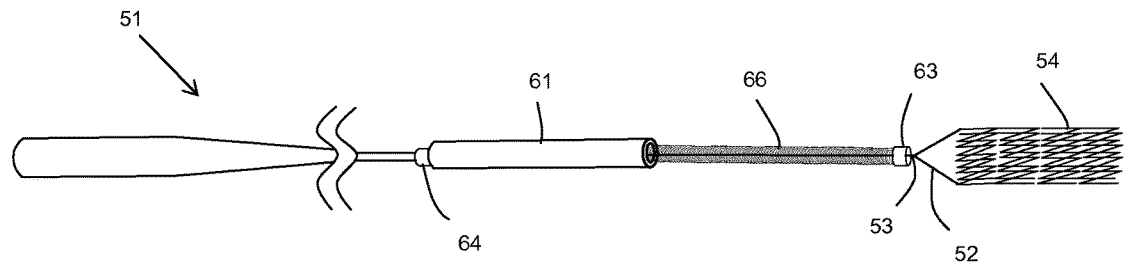
FIG. 2 is a detailed illustration of the clot retrieval system of the present invention.

FIG. 2 is a detailed illustration of a clot retrieval device of the present invention. The slider tube design described in FIG. 2 avoids vessel damage without the risk of inadvertent device retraction into the microcatheter. The device 51 has an elongate shaft 53 having a distal end that extends interior of the artery and a proximal end that extends exterior of the artery, a clot engaging body 54 configured at the distal end of the elongate shaft, tethers 52 having distal ends connected to the proximal end of the clot engaging body 54 and proximal ends connected to the elongate element 53. A coil 66 is slidably disposed around the elongate member 53, the distal end of which is located proximal of a distal stop 63 and the proximal end is located within the lumen of a slider tube 61. The tubular member 61 is slidably disposed around the elongate shaft 53. The distal end of the slider tube 61 extends over the coil 66 and the proximal end is located distal of the proximal stop 64. The slider tube itself may comprise a range of constructions, some of which are shown in FIGS. 4 to 10. The slider tube 61 is preferably a solid tube composed of flexible material such that it may be retracted through tortuous vasculature without deforming it. In one preferred embodiment the slider tube 61 is composed of a polymer such as PEN, PET, UHMWPE, LCP or Aramid.

In a preferred embodiment the elongate member 53 has a lower coefficient of friction while being retracted through the slider tube 61 when compared to that between the slider tube and the vessel. As a result, the slider tube 61 remains in situ as the elongate shaft 53 is retracted and during dislodgment of the clot thereby protecting the walls of the vessel from abrasion.

The overall effect of the slider tube 61 is to spread the pressure and tension that the elongate member 53 normally exerts on the vessel across the entire surface area of the tube 61 thus reducing the tension from accumulating in any one particular area in the vessel.

In addition, the use of a slider tube 61 is a more secure form of prevention of abrasion than a microcatheter. If the microcatheter was used in an effort to prevent abrasion of the inner walls of the vessel the device may potentially re-enter the microcatheter. If this occurred the device would compress into its collapsed configuration and it may lose control of the clot. The clot would then be free to travel to the more distal vasculature and occlude a smaller vessel with potentially catastrophic consequences. As the distal stop 63 and the slider tube 61 are located between the device 51 and the microcatheter this occurrence is prevented.

Figure 3A:
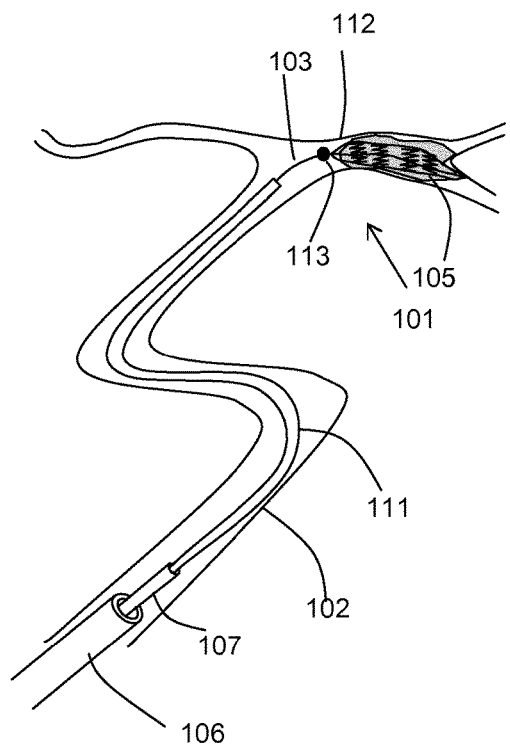
FIG. 3a shows a novel method for clot retrieval.
Figure 3B:
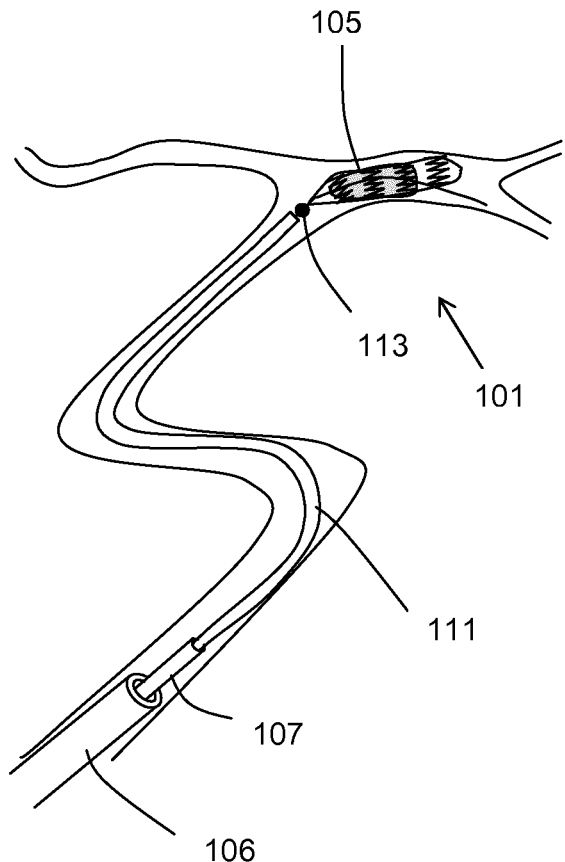
FIG. 3b shows the retrieval of clot using the present invention.
Figure 4:
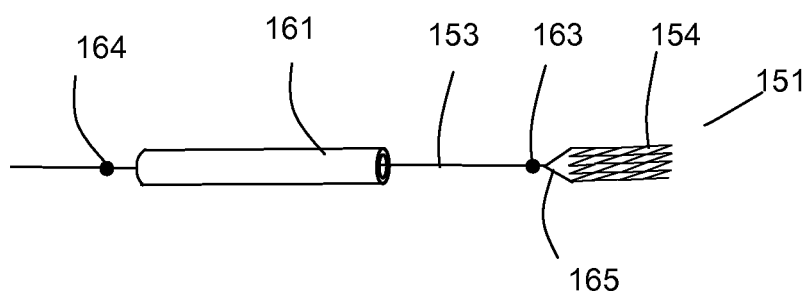
FIG. 4 shows alternative embodiments of the present invention with stops.

FIG. 3*a-b* illustrates the preferred method of retrieving a clot from tortuous vasculature using the present invention. A guidewire 103 and microcatheter 107 are inserted into the artery and are advanced across the occlusive clot 105, which is lodged at a bifurcation using any conventionally know techniques. The guidewire 103 is removed from the microcatheter to allow the clot retrieval device 101 to be advanced within the microcatheter in a collapsed configuration until it is located within the clot. The device 101 is deployed on retraction of the microcatheter 107. The device has an elongate shaft 103, having a distal end that extends interior of the artery and a proximal end that extends exterior of the artery. On expansion, the device exerts a radial force upon the clot 105 and captures the clot against the lumen of the vessel 102.

On further retraction of the microcatheter 107, the distal stop 113 is deployed. This is followed by the deployment of a slider tube 111 and a distal stop. The distal and proximal stops are connected to the elongate member 103 at the distal and proximal ends of the slider tube 111. The tubular member 111 is slidably disposed along the elongate member 103. Upon the deployment of the slider tube 111, the clot retrieval device 101 is then retracted proximally by means of the elongate member 103. The device 101 is retracted until the distal stop reaches the distal end of the slider tube 111. When it reaches the slider tube 111, the slider tube 111 is automatically withdrawn as the clot retrieval device 101 and the clot 105 are withdrawn proximally into the guidecatheter 106.

FIG. 4*a* illustrates another alternative embodiment of the present invention. The device 151 in this case having distal end that extends interior of the artery and a proximal end that extends exterior of the artery, a clot engaging body 154 and control tethers 165. The distal ends of the control tethers are attached to the proximal end of the engaging body 154 and the proximal ends are attached to the distal end of the elongate member 153.

The slider tube 161 is slidably disposed around the elongate member 153. The distal stop 163 is affixed to the distal end of the elongate member 153. The proximal stop 164 is affixed to the elongate member proximal of the slider tube 161. The slider tube 161 is held in place by the distal 163 stop and the proximal stop 164. The device 151 is advanced through the microcatheter in a collapsed configuration until it is within the clot. Once the device is deployed it expands and captures the clot by exerting a radial pressure on the clot. As the device is being retracted, the slider tube 161 is automatically withdrawn as the clot retrieval device 151 is withdrawn proximally into the guidecatheter.

Figure 5:
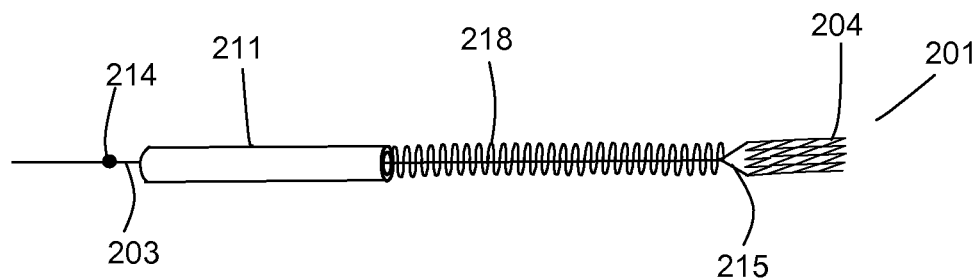
FIG. 5 shows alternative embodiments of the present invention with a spring.

FIG. 5 illustrates another alternative embodiment of the present invention. The device 201 having a distal end that extends interior of the artery and a proximal end that extends exterior of the artery, a clot engaging body 204 and control tethers 215. The distal ends of the control tethers 215 are attached to the proximal end of the engaging body 204 and the proximal ends are attached to the distal end of the elongate member 203. A slider tube 211 contains the elongate member 203 at the distal end of the elongate member 203. The device contains a spring 218 having distal ends attached to the distal end of the elongate member 203 and proximal end attached to the elongate shaft distal. In this embodiment of the invention, there is no requirement for a distal stop as the spring 218 functions as a distal stop. As the clot retrieval device is retracted the slider tube 211 automatically begins to withdraw as soon as the proximal end of the spring 218 contacts the distal end of the slider tube 211.

In the preferred embodiment the spring 218 is a soft spring and therefore the spring 218 also has the effect of reducing the tension between the device 201 and the elongate member 203 and the slider tube 211 during retraction of the device 201. The proximal stop 213, which is located at the proximal end of the slider tube 211, prevents the slider tube 211 from retracting further into the microcatheter upon deployment.

Figure 6:
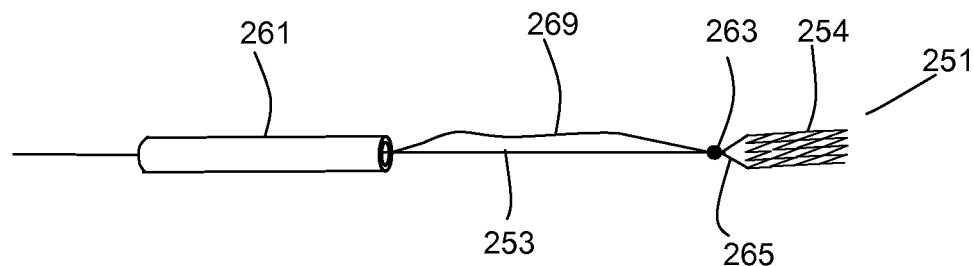
FIG. 6 shows alternative embodiments of the present invention with a tether.

FIG. 6 illustrates another alternative embodiment of the present invention. A clot retrieval device 251 has a distal end that extends interior of the artery and a proximal end that extends exterior of the artery, a clot engaging body 254 and control tethers 265. The distal ends of the control tethers 265 are attached to the proximal end of the engaging body 254 and the proximal ends are attached to the distal end of the elongate member 253. A slider tube 261 is slidably disposed around the elongate member 253 at the distal end of the elongate member 253. A distal stop 263 is located at the distal end of the elongate member 253. An elongate tether 269, having distal end affixed to the distal end of the elongate member 253 and proximal of the distal stop and proximal end attached to the slider tube 261, has the effect of tying the slider tube 261 to the device while allowing it to move within the vasculature thus reducing the overall friction of the device during retraction. The elongate tether 269 functions as a proximal stop for the slider tube.

Figure 7:
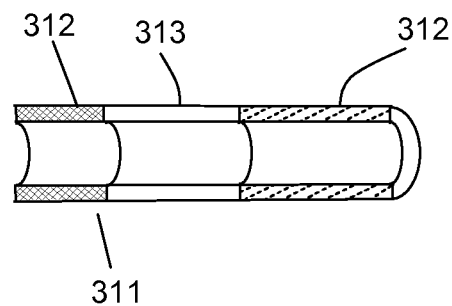
FIG. 7 shows an isometric view of an alternative embodiment of the present invention with stiff and rigid sections.

FIG. 7 is an isometric view of a section of an alternative embodiment of this invention. A slider tube 311 comprises an atraumatic design wherein alternative sections of the tube are composed of regions of stiff material 312, which are punctuated by flexible joint regions or articulation regions 313. This design allows the tube to articulate with the vasculature without distorting the vessels or causing abrasion to the walls of the vessels. The slider tube 311 is slidably disposed around the elongate member and contains the elongate member during retraction and prevents it from causing abrasion or distorting the vessels. This embodiment also reduces the compression of the vessels proximal of the device. Any number of flexible joints and stiff regions can be used at any section along the tube and can be used in conjunction with any tubular device disclosed elsewhere in this document.

Figure 8A:
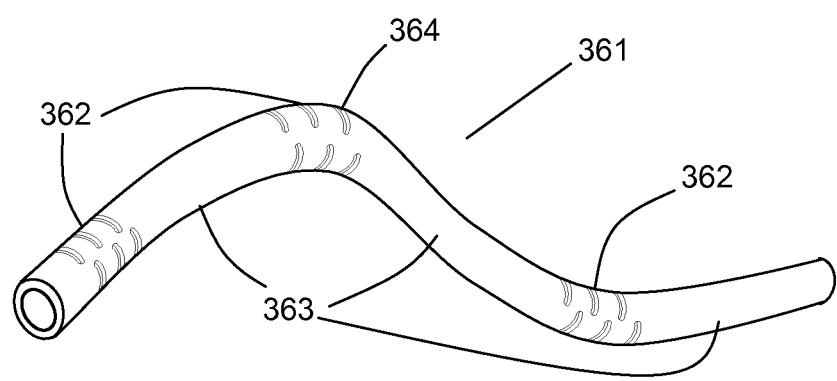
FIG. 8a shows alternative embodiments of the present invention with flexible sections.
Figure 8B:
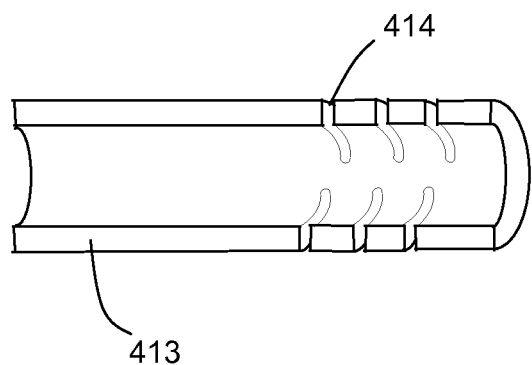
FIG. 8b shows detail of the device of FIG. 8a in isometric view.

FIG. 8*a* is an isometric view of a section of an alternative embodiment of the present invention. A slider tube 361 comprises an atraumatic design wherein the tube is punctuated by flexible regions 362 alternated with rigid regions 363. The flexible regions 362 are composed of sections of tubing in which sections of the tubing have been removed. These slits 364 allow the slider tube to be more flexible as it reduces the outer surface area of the tube and allows it bend at smaller angles. During retraction this reduces the effect of abrasion of the vessels and prevents distortion and compression of the vessels proximal of the device thus enhancing the device performance. FIG. 8*b* is an isometric view of the slits 414 in the slider tube 411. The slits may be of any shape and size and number and they may be located at any section across the tube. Such slits may be used in conjunction with any other tubular designs disclosed elsewhere in this document.

Figure 9:
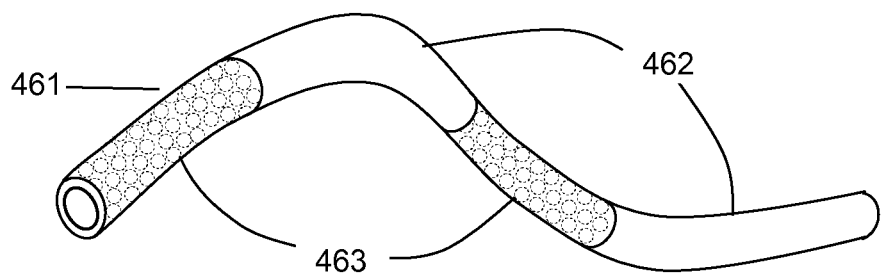
FIG. 9 shows alternative embodiments of the present invention with sections of varying friction.

FIG. 9 is an isometric view of a section of an alternative embodiment of the present invention. A slider tube 461 is comprised of an atraumatic design wherein the tube is comprised of alternating low friction regions 462 and high friction regions 463. The low friction regions may be created by electropolishing the tube to obtain a smooth outer surface and the high friction regions may be created by fashioning slight protrusions which emanate from the outer surface of the tube. The protrusions may be of any shape or size or number. In the preferred embodiment the effect of the varying regions of high and low friction would be to spread the pressure and tension that the elongate member exerts on the vessel across the entire surface area of the tube thus reducing the tension from accumulating in any one particular area in the vessel. The slight increase in friction of these alternating regions will increase the efficiency of the elongate element as it moves through the slider tube. This effect is due to the higher coefficient of friction between the slider tube and the vessel compared to the lower coefficient between the elongate element and the slider tube. The result is that the slider tube remains in situ as the elongate shaft is retracted thus protecting the vessel walls from abrasion. Any number of low friction regions and high friction regions can be used at any section along the tube and can be used in conjunction with any tubular device disclosed elsewhere in this document.

Figure 10:
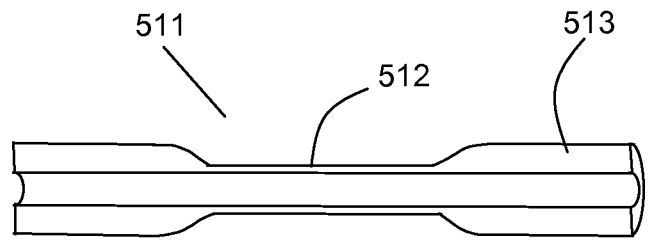
FIG. 10 shows alternative embodiments of the present invention with sections of varying diameter.
Figure 11A:
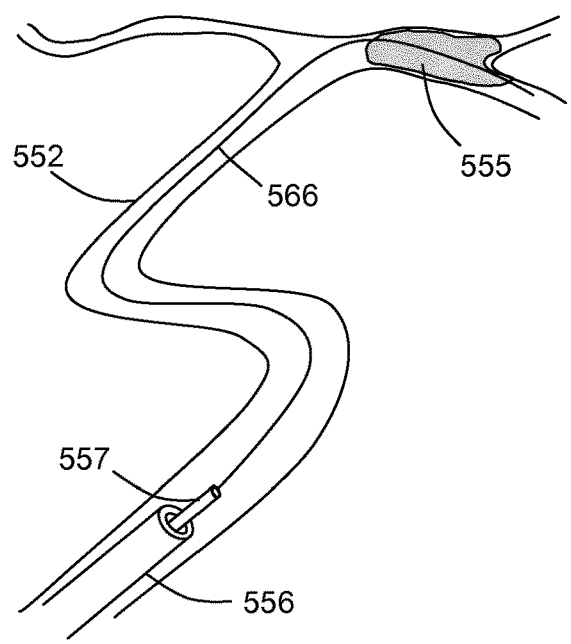
FIG. 11a shows the method of use of the clot retrieval system of the present invention.
Figure 11B:
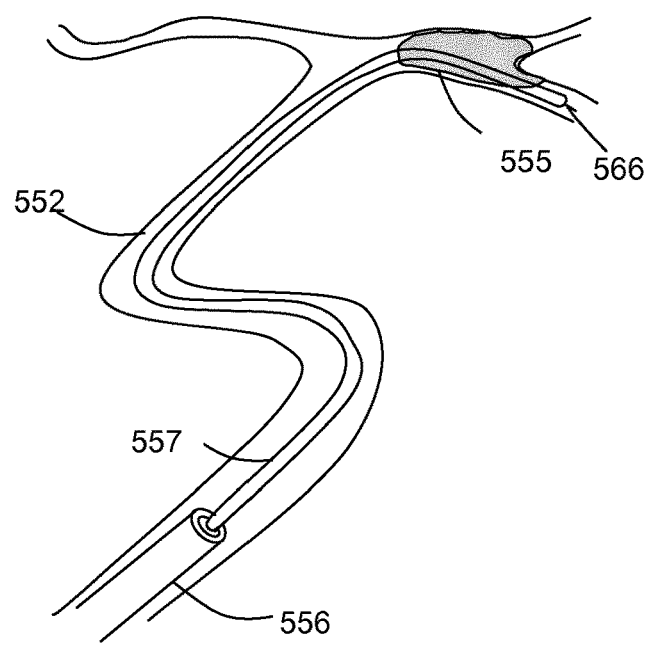
FIG. 11b illustrates a microcatheter being advanced in a vessel.
Figure 11C:
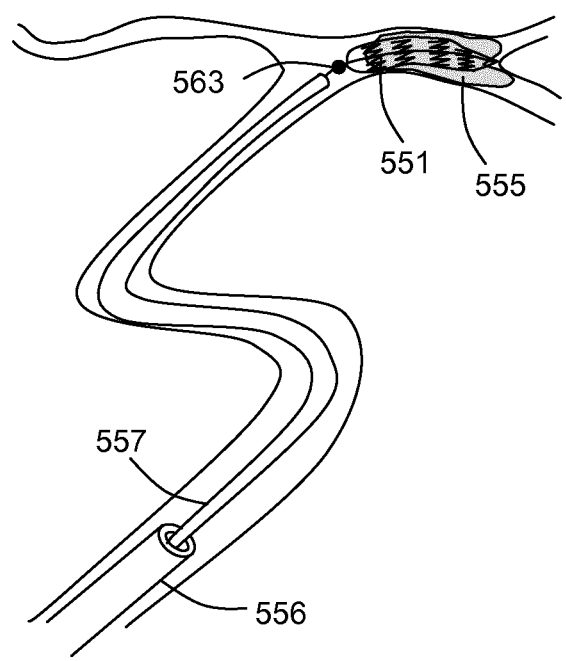
FIG. 11c illustrates the clot retrieval device expanding within a clot.
Figure 11D:
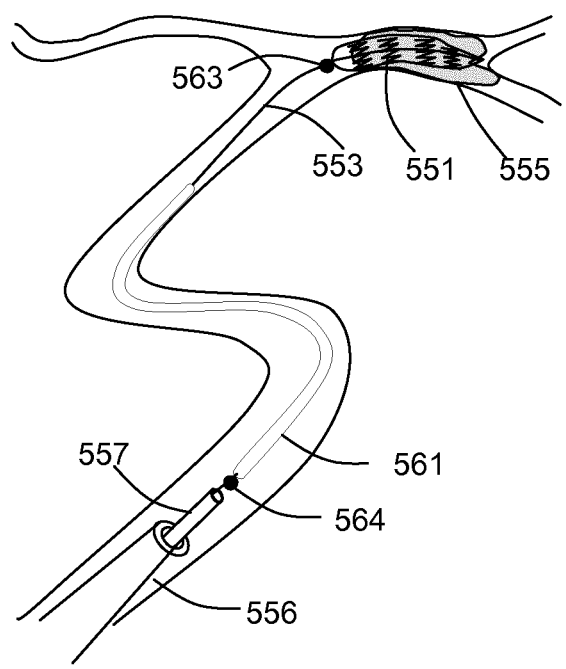
FIG. 11d illustrates the microcatheter being retracted and the slider tube being deployed.
Figure 11E:
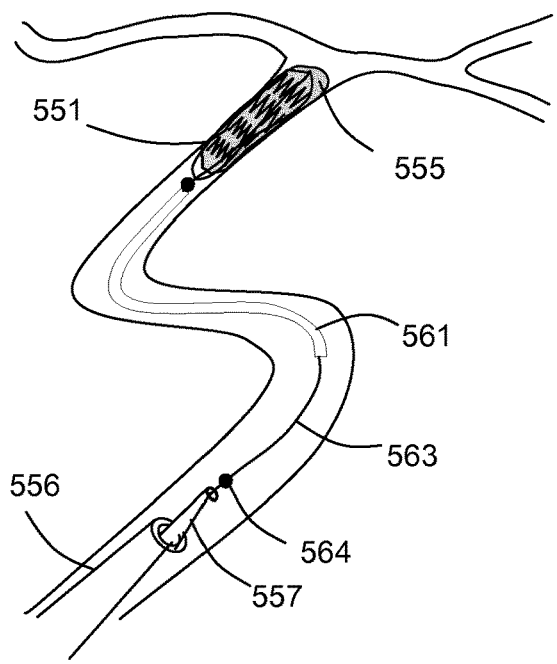
FIG. 11e illustrates the clot retrieval device being stopped by the distal mechanical stop and the slider tube.
Figure 11F:
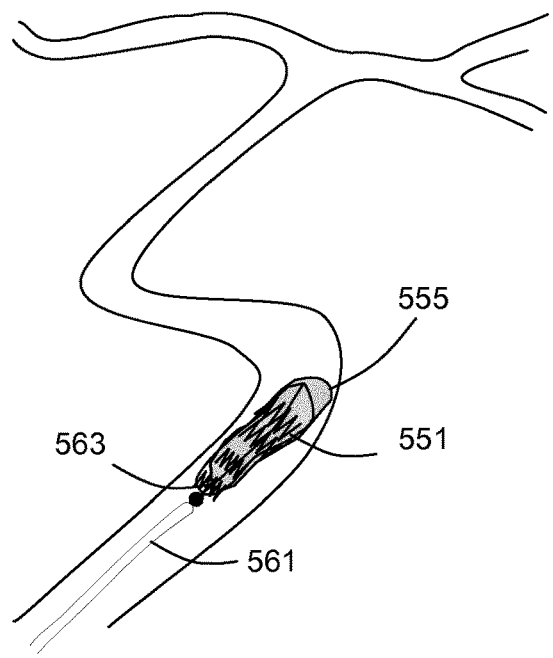
FIG. 11f illustrates the slider tube and the clot retrieval device and the clot being retracted.

FIG. 10 is an isometric view of a section of an alternative embodiment of the present invention wherein a slider tube 511 is composed of regions of small 512 and large diameter 513. The regions of small diameter 512 may alternate with regions of large diameter 513 thus creating a low profile device. The atraumatic design reduces the force and tension on the vasculature as it increases the flexibility of the tubular device and it decreases the risk of abrasion. In the preferred embodiment the effect of the varying regions of smaller and larger diameter would be to spread the pressure and tension that the elongate member exerts on the vessel across the entire surface area of the tube thus reducing the tension from accumulating in any one particular area in the vessel. Any number of small diameter regions and large diameter regions can be used at any section along the tube and can be used in conjunction with any tubular device disclosed elsewhere in this document.

Use of a slider tube of the present invention in conjunction with a clot retrieval device of the present invention in removing an obstructive clot 555 from an intracranial artery 552 is depicted in FIG. 11a-f. A guidewire 566 and microcatheter 557 are inserted in the artery 552 by means of a guidecatheter 556 and are advanced across an obstructive clot 555 using any conventionally known techniques. The guidewire 566 is removed from the microcatheter 557 to allow the clot retrieval device 551 and the slider tube 561 to be advanced through the microcatheter in the collapsed configuration until the clot retrieval device 551 is within the clot 555. The device has an elongate shaft 553, having a distal end that extends interior of the artery and a proximal end that extends exterior of the artery, distal stop 563 which is located at the proximal end of the ring elements and proximal stop 564 which is located at the proximal end of the slider tube 561. It has a clot engaging body 554 which is connected to the elongate element 553.

The microcatheter 557 is retracted to deploy the clot retrieval device 551 within the clot in a manner that the engaging portion of the clot retrieval device is positioned across the clot. The engaging section of the clot exerts a gentle radial force on the clot while maintaining the integrity of the clot and avoiding its dissection. The microcatheter 557 is then further retracted proximally to deploy the mechanical stops 563 and 564 and the slider tube 561 within the vessel 552. Once the clot retrieval device 551 has engaged the clot 555 the device 551 is retracted proximally by means of the elongate 30 member 553 to which the device is affixed. The device is retraced proximally until the distal stop 563 makes contact with the slider tube 561. When the distal stop 563 has contacted the slider tube 561, the slider tube 561 will automatically be withdrawn as the device 551 and the microcatheter 557 are withdrawn proximally into the distal end of the guidecatheter 556.

During this process the tension and the force that the elongate element 553 would normally exert on the inner lining of the vessel is absorbed by the slider tube 561 and spread across the entre outer surface of the slider tube 561. Therefore the slider tube prevents excessive distortion of the vessel and prevents abrasion of the inner walls of the vessel.

Furthermore, the slider tube 561 is a more secure form of prevention of abrasion when compared to a microcatheter 557. If the microcatheter 557 was used in the manner of a slider tube 561, the device 551 may unintentionally withdraw into the microcatheter. Should this happen the device 551 would compress into its collapsed configuration and the clot 555 would escape from the device and leaving open the possibility that it might advance distally through the vessel and occlude a smaller vessel at another junction in the vasculature. As the slider tube 561 and the mechanical stops 563 and 564 are located between the device 551 and the microcatheter 557 this reduces the possibility of this occurring.

The slider tube 561 may be comprised of slits or rigid and flexible regions and/or high and low friction regions or any combination of the above as disclosed elsewhere in this document. It may be attached to the elongate member by the means described previously such as by a tether or a spring. It may also be held in situ around the elongate member by proximal and/or distal stops. Preferably the slider tube 561 is composed of a polymer such as PEN, PET, UHMWPE, LCP or Aramid. The slider tube 561 may be used in conjunction with any mechanical thrombectomy device such as Stentrievers.

Modification and additions can be made to the embodiments of the invention described herein without departing from the scope of the invention. For example, while the embodiments described herein refer to particular features, the invention includes embodiments having different combinations of features. The invention also includes embodiments that do not include all of the specific features described.

The invention is not limited to the embodiments hereinbefore described which may be varied in construction and detail.

The invention claimed is:

1. A clot retrieval system comprising:
   a clot retrieval device;
   a catheter; and
   a tubular shield element comprising an outer diameter ranging between 0.010 inch to 0.026 inch;
   the clot retrieval device comprising an elongate member having a proximal end and a distal end, and a clot engaging element at the distal end of the elongate member the clot engaging element having a collapsed delivery configuration and an expanded deployed configuration,
   the catheter being adapted for placement at a location at which a distal end of the catheter is proximal of the clot engaging element,
   the tubular shield element extending over the elongate member and being adapted for location between the distal end of the catheter and the proximal end of the clot engaging element and being movable relative to the elongate member when the clot engaging element is in the expanded configuration so that a retraction force applied to the elongate member is spread over an outer surface of the tubular shield element.

2. A clot retrieval system as claimed in claim 1 wherein the tubular shield element is slidable relative to the elongate member.

3. A clot retrieval system as claimed in claim 2 wherein the elongate member comprises a distal stop and a proximal stop to limit the sliding movement of the tubular element.

4. The clot retrieval system as claimed in claim 2 wherein the tubular shield element comprises a distal abutment surface and a proximal abutment surface.

5. The clot retrieval system as claimed in claim 1 wherein the tubular shield element comprises an inner lumen and an outer surface, the inner lumen being sized to slide freely over at least a distal portion of the elongate member.

6. The clot retrieval system as claimed in claim 1 wherein the tubular shield element inner lumen comprises a first material and the tubular element outer surface comprises a second material.

7. The clot retrieval system as claimed in claim 6 wherein the tubular shield element first material comprises a lower coefficient of friction than the tubular element second material.

8. The clot retrieval system as claimed in claim 1 further comprising a microcatheter for delivery of the clot engaging element in the collapsed configuration.

9. The clot retrieval system as claimed in claim 8 wherein the lumen of the microcatheter is configured to receive the tubular shield element.

10. The clot retrieval system as claimed in claim 9 wherein the outer diameter of the tubular element is at least as small as the diameter of the clot engagement element in its collapsed configuration.

11. The clot retrieval system as claimed in claim 1 wherein the outer diameter is at least 0.012 inch.

12. The clot retrieval system as claimed in claim 1 wherein the outer diameter is not more than 0.020 inch.

13. The clot retrieval system as claimed in claim 1 wherein the outer diameter ranges between 0.014" to 0.019 inch.

* * * * *